US009649096B2

(12) United States Patent
Sholev (10) Patent No.: US 9,649,096 B2
(45) Date of Patent: May 16, 2017

(54) MOTORIZED SURGICAL INSTRUMENTS (75) Inventor: Mordehai Sholev, Moshav Amikam (IL)

(73) Assignee: Human Extensions Ltd., Netanya (IL)

(*) Notice: Subject to any disclaimer, the term of this patent is extended or adjusted under 35 U.S.C. 154(b) by 463 days.

(21) Appl. No.: 14/006,111

(22) PCT Filed: Mar. 21, 2012

(86) PCT No.: PCT/IL2012/000123
§ 371 (c)(1),
(2), (4) Date: Oct. 4, 2013

(87) PCT Pub. No.: WO2012/127462
PCT Pub. Date: Sep. 27, 2012

(65) Prior Publication Data
US 2014/0025089 A1 Jan. 23, 2014

Related U.S. Application Data (60) Provisional application No. 61/466,025, filed on Mar. 22, 2011.

(51) Int. Cl.
A61B 17/00 (2006.01)
A61B 17/29 (2006.01)
A61B 34/00 (2016.01)

(52) U.S. Cl.
CPC ........ *A61B 17/00234* (2013.01); *A61B 17/29* (2013.01); *A61B 17/2909* (2013.01); *A61B 34/70* (2016.02); *A61B 34/72* (2016.02); *A61B 34/74* (2016.02); *A61B 34/76* (2016.02); *A61B 2017/00398* (2013.01); *A61B 2017/00438* (2013.01); *A61B 2017/00442* (2013.01); *A61B 2017/2901* (2013.01); *A61B 2017/2927* (2013.01); *A61B 2017/2929* (2013.01); *A61B 2034/741* (2016.02)

(58) Field of Classification Search
CPC .............. A61B 17/00234; A61B 17/29; A61B 17/2909; A61B 19/22; A61B 2017/2901; A61B 2017/2927; A61B 2017/2929; A61B 2017/00398; A61B 2017/00438; A61B 2017/00442; A61B 34/72; A61B 34/74; A61B 34/76; A61B 2034/741
See application file for complete search history.

(56) References Cited

U.S. PATENT DOCUMENTS 5,716,352 A * 2/1998 Viola ............... A61B 17/00234
128/898
5,792,165 A 8/1998 Klieman et al.
6,263,755 B1 7/2001 Perlin
7,208,005 B2 4/2007 Frecker et al.
(Continued)

OTHER PUBLICATIONS

International Search Report dated Aug. 27, 2012, in corresponding International Application No. PCT/IL2012/000123.

*Primary Examiner* — Corrine McDermott
*Assistant Examiner* — Tin Nguyen (57) ABSTRACT A motorized surgical instrument that may be held by the surgeon or be attached to the surgeon's limb via a special adapter that includes an interface between the surgeon and the surgical tool is provided. The motorized surgical instrument includes mechanism, motors, gears, interface and power source that enable the surgeon to easily control the motorized surgical tools in order perform the surgical procedure.

4 Claims, 10 Drawing Sheets (56) References Cited

U.S. PATENT DOCUMENTS

| | | |
|---|---|---|
| 7,837,687 B2 | 11/2010 | Harp |
| 7,896,893 B2 | 3/2011 | Laufer et al. |
| 2012/0089131 A1 | 4/2012 | Zemlok et al. |

* cited by examiner

MOTORIZED SURGICAL INSTRUMENTS

FIELD OF THE INVENTION

The present invention relates to the field of remotely manipulated surgical tools, generally for laparoscopic surgery, especially such tools having motorized motions in several degrees of freedom.

BACKGROUND OF THE INVENTION

In laparoscopic surgery, the surgeon performs the operation through small incisions made in the patient's body cavity, using long instruments and observing the internal anatomy and the progress of the surgical procedure with an endoscope camera. Such surgical tools are conventionally held manually by the surgeon, often using both hands, and the instruments are generally activated by the power of the surgeon's bare hands, in much the same way as regular surgical instruments used for conventional surgery, are operated.

To overcome these problems, several surgical tools have been developed, But these technologies are often uncomfortable to use, may limit the dexterity of the surgeon and Relatively to the required action.

SUMMARY OF THE INVENTION

The present invention seeks to present a novel surgical tool mechanism and interface for activating surgical instruments, useful for performing laproscopic surgical procedures on a patient's body. The system incorporates a surgical tool or effector having both articulated joints and rotations, and differs from prior art instruments in that the actuation is powered by means of electric motors driving combinations of gears and actuating mechanisms. The system is constructed to simulate the motions that would be made by a manually-held, equivalently functional tool. The system comprises a body that includes motors, gears and a power source; mechanisms which enable change of the spatial position of the surgical tool's component parts; and a mechanism which enables control of the surgical tool end effector. The motion is preferably transmitted by means of rotation of small diameter concentric hollow tubes, connected at their proximal ends to a gear housing, and connected at their distal ends to either an end effector, or to a second set of articulately joined concentric hollow tubes. According to one embodiment, the connections between two tubes sets enables transmitting rotation power from one set of tubes to the other simultaneously. Other connections between the tube sets enable transmitting angular moments from one set of tubes to the other simultaneously. The end effector is connected at the distal part of the last set of tubes. The motorized surgical body may be held by the surgeon in various ways—either by directly holding the motorized surgical tool body, or by means of an adapter that enables the surgeon to connect the motorized surgical tool to his limbs or other parts of his body.

The use of motorization in the present invention reduces muscular fatigue in the surgeons hands or arms, since the tool motions are performed under power. Prior art robotic surgical tools overcome the problem of muscular fatigue, but the motions required by the surgeon at the operating interface are often unnatural compared with the tactile feeling when using an equivalent manual tool. Furthermore, prior art robotic systems are generally based on full size anthropomorphic robots, which are generally of such a size that the surgeon cannot get sufficiently close to the patient to view the operation from close-up. The arrangement of the present invention, and in particular, its small physical dimensions, allows close personal contact of the surgeon with the patient.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
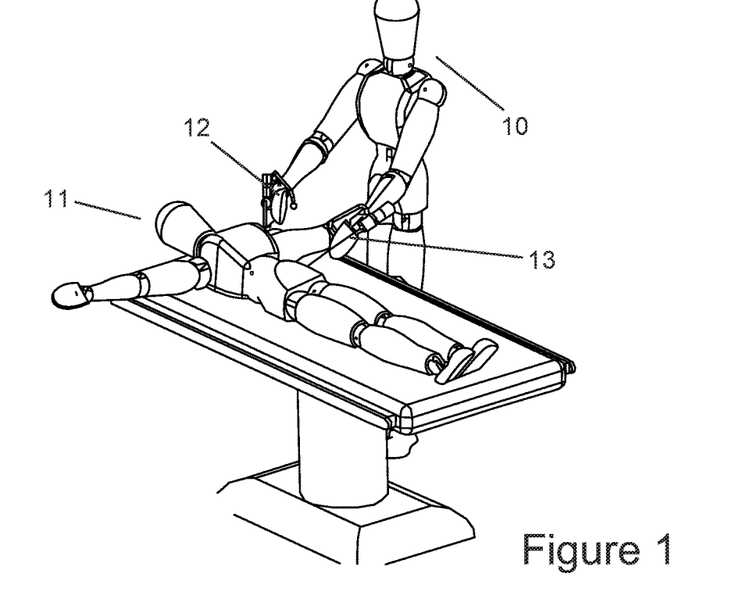
FIG. 1 illustrates schematically a surgeon performing a laparoscopic procedure on a patient in the operating room, using a first preferred embodiment of the system of the present invention.

Reference is now made to FIG. 1, which illustrates schematically a surgeon 10 performing a laparoscopic procedure on a patient 11 in the operating room, using a first preferred embodiment of the system of the present invention. The system is characterized in that the surgeon's hands 12, 13, are able to grip and manipulate the robotic interface handles in a manner close to the way in which manually held instruments performing the same procedure would be gripped and manipulated by the surgeon. The interface of the tools of the present system thus imitates the motion of the hands of the surgeon, and uses similar, if not the same, motions and muscles. The system can preferably utilize several different tools for different functions, which can be readily changed during the surgical procedure with change in the surgical tasks to be performed. Alternatively and preferably, the basic tool motion transmission mechanism can be standardized, and different heads used for different motion or actuation functions.

Figure 2:
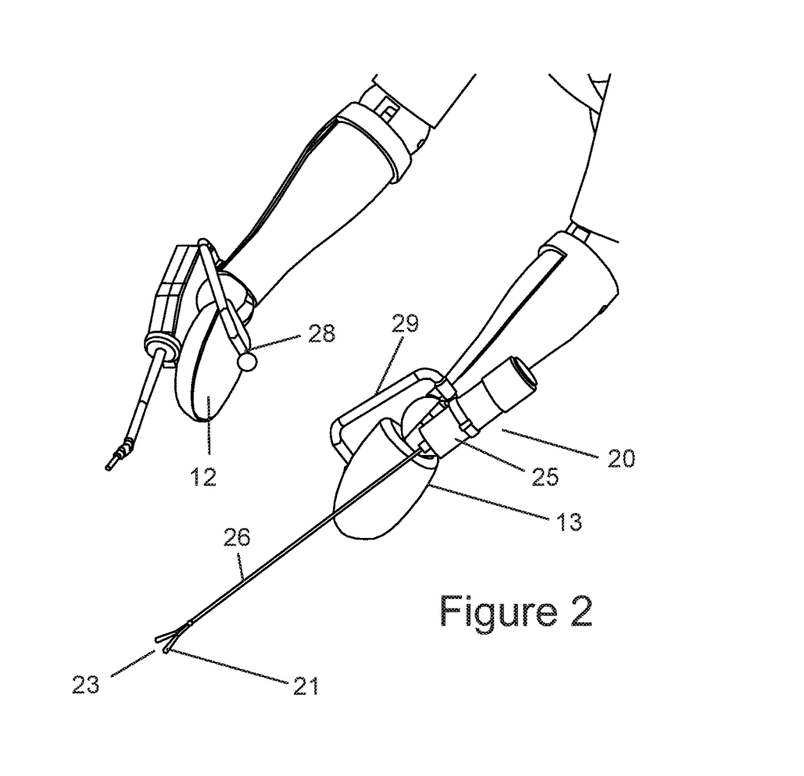
FIG. 2 is a close-up schematic view of the set of motorized surgical tools shown in FIG. 1.

Reference is now made to FIG. 2, which is a close up schematic view of the set of motorized surgical tools shown in FIG. 1, held in the surgeon's hands 12, 13 by operating arms 28, 29. The tool 20 in the surgeon's left hand is a grasper 21. In this embodiment, three degrees of freedom (DOF) of motion are available, namely the rotation 22 of the grasper, its opening and closing action 23, and the linear motion 24 of the actuating rod 26 along the direction of the length of the tool. The first two motions are power-implemented by the tool's motors and gears, housed in the motor casing 25, while the third, linear motion is implemented by the surgeon's own manual moving of the whole tool using motion of his hand. It is to be understood that further degrees of motion are also possible, such as angular tilt in any direction, since the tool is held in the surgeon's hand, which can move freely in space. However, such further degrees of freedom are likely to be largely limited in practice by the constrained surgical environment in which the tool is being used. Further details of the operation of this tool are given hereinbelow in FIGS. 10 to 16, and associated description.

Figures 3, 4:
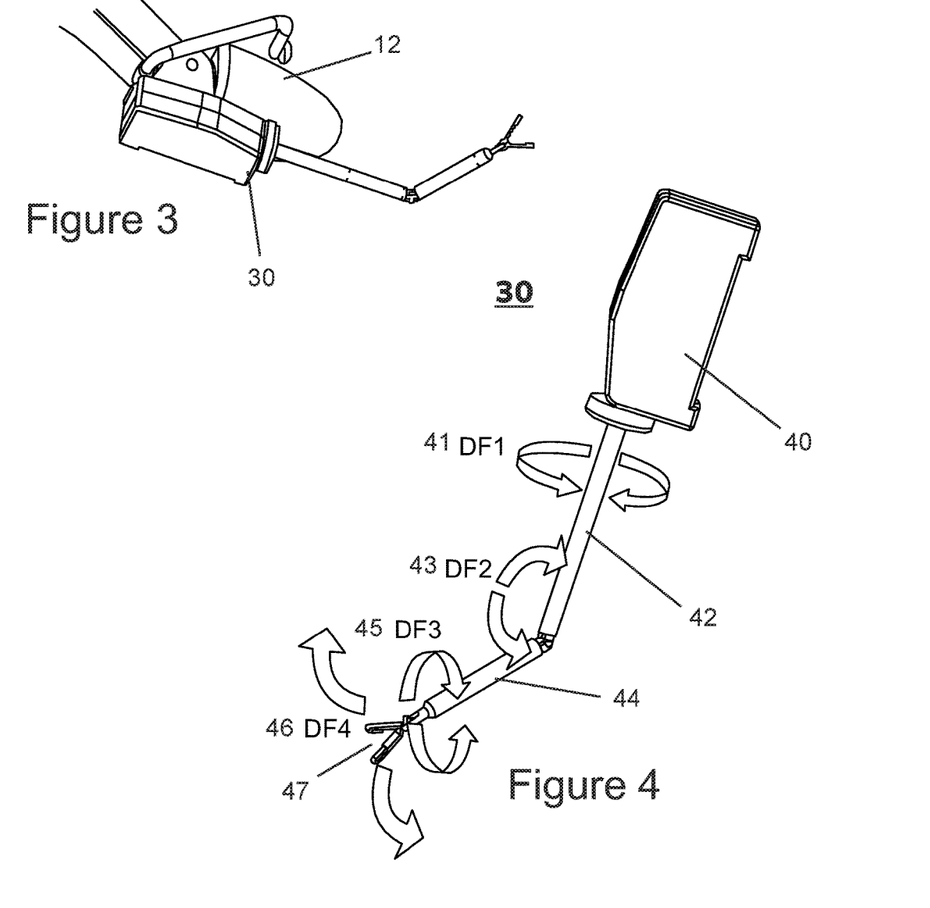
FIG. 3 is a close up schematic view of the motorized surgical tool, according to another preferred embodiment of the present invention, held in the surgeon's right hand of FIGS. 1 and 2.
FIG. 4 shows a first kind of motorized surgical tool and its degrees of freedom

Reference is now made to FIG. 3, which is a close up schematic view of the motorized surgical tool, according to another preferred embodiment of the present invention, held in the surgeon's right hand 12 of FIGS. 1 and 2. This tool 30 also has a grasper at its extremity, but in this case includes an articulated arm, such that unlike the embodiment in FIG. 2, it has 4 degrees of freedom.

Reference is now made to FIG. 4, which is a view of the tool 30 of FIG. 3, showing the motions provided by this embodiment. The motions originate in the gear box 40, which contains the motors and transmission gears for generating the movements needed for the tool functions. The first DOF, 41, designated DF1, is a rotationary motion of the upper arm 42 of the tool. The second DOF 43, designated DF2, is a bending motion between the upper arm 42 of the tool and the lower arm 44. The third DOF 45, designated DF3, is a rotationary motion of the lower arm 44 of the tool. The final DOF 46, designated DF4, is the actuation of the opening and closing of the grasper end effector 47. A combination of all of these motions enables a high level of flexibility to be achieved with this tool, even without taking into account any additional movement or orientation supplied by manual motion of the surgeon's hand. The operation of the motion actuators of the tool of the embodiment of FIG. 4 is further explained in FIGS. 6 to 9B.

Figure 5:
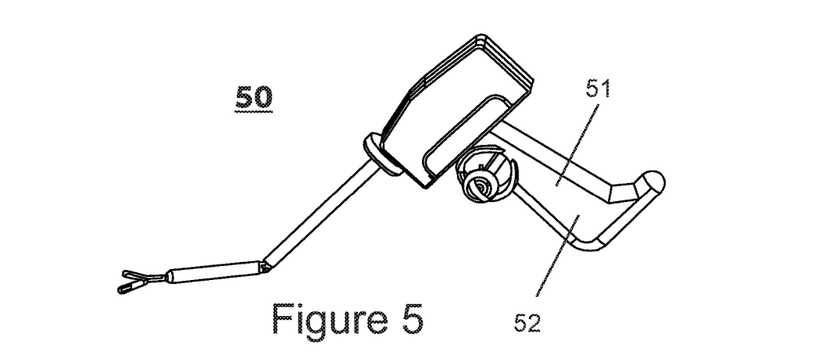
FIG. 5 illustrates a motorized surgical tool, similar to that shown in FIG. 4, but equipped with a grip handle and a battery cavity.

Reference is now made to FIG. 5, which illustrates schematically a motorized surgical tool 50, similar to that shown in FIG. 4, but equipped with a grip handle 51 and a battery cavity 52, such that it can be directly hand-held by the surgeon and used as an independent tool. It is to be understood that this option can be applied to any of the motorized surgical tool preferred embodiments described herewithin.

Figure 6:
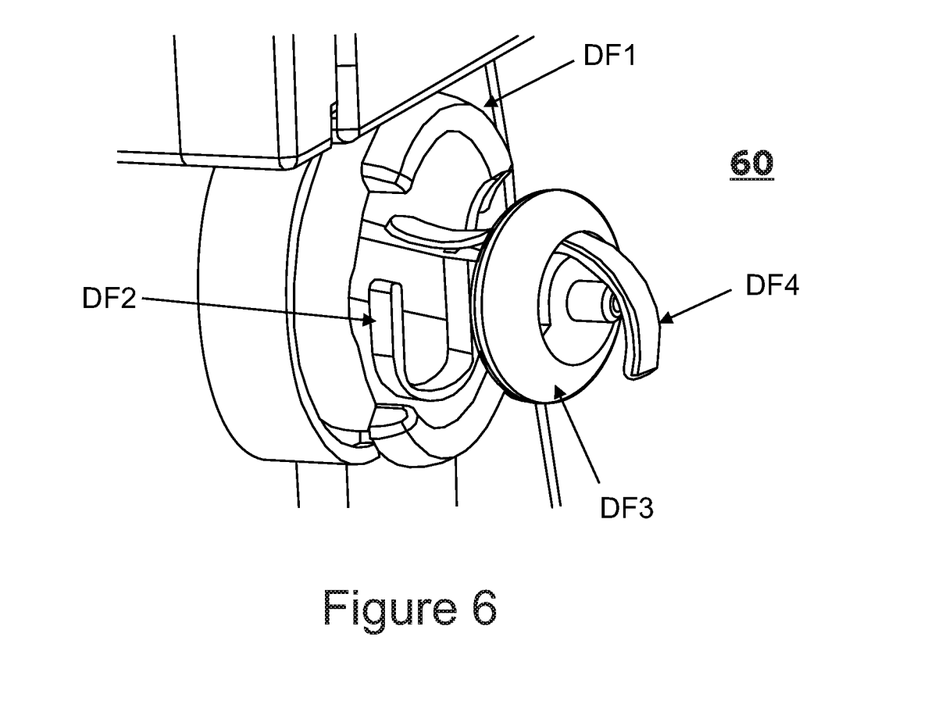
FIG. 6 illustrates schematically a preferred interface for the motorized surgical tool of FIG. 4, showing the positions of the controls for each degree of freedom.

Reference is now made to FIG. 6, which illustrates schematically, according to a further preferred embodiment of the present invention, an interface 60 for the motorized surgical tool of FIG. 4, showing the positions of the controls for each degree of freedom. The interface is held in the surgeon's hand, such that simple access to each of the motion controls can be obtained. Rotation of the upper arm is achieved by rotation of the finger control marked DF1. Rotation of the lower arm is achieved by rotation of the knob marked DF3. Bending of the arm joint is accomplished by backward and forward motion of the thumb hook marked DF2. Closing of the grasper is achieved by pressure on the trigger marked DF4, preferably using the base of the palm of the hand. Each of the interface controls is preferably connected to a rotary or sliding potentiometer, whose output signal is used for controlling the motor responsible for that particular motion. If the grasper is a two-position tool, i.e. either open or closed, the trigger DF4 will preferably operate a microswitch to open or close the grasper. If the grasper's jaws can be continuously adjusted between open and closed, then a potentiometer type of input control is preferably used at the interface. It is to be understood that the control interface shown in FIG. 6 is only one possible embodiment, and that the invention is not meant to be limited by the particular combination shown in FIG. 6.

Figure 7:
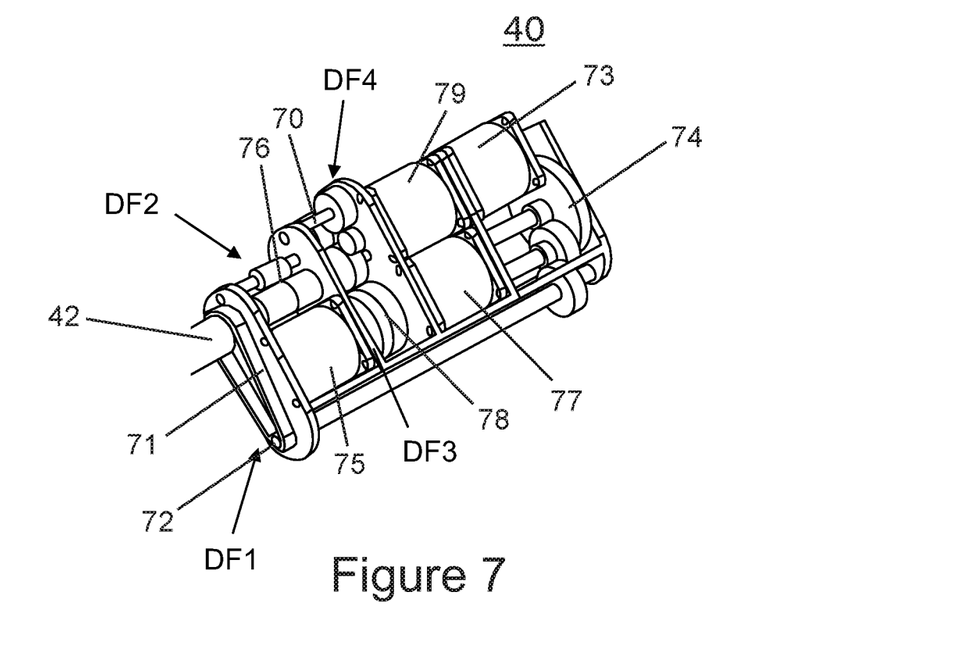
FIG. 7 illustrates schematically, an internal view of the gear box of the tool of FIGS. 3 to 5.

Reference is now made to FIG. 7, which illustrates schematically, according to a further preferred embodiment of the present invention, an inside view of the gear box 40 of the tool of FIGS. 3 to 5, showing a preferred arrangement of the motors and transmission gears for generating the movements needed for the tool functions. Motion DF1, rotation of the upper arm, is transmitted to the upper arm outer tube 42, by means of the belt drive 71, driven by shaft 72, which receives its drive from electric motor 73 through gear train 74. Bending motion DF2 of the articulated arm is provided from motor 75 though the gear train 76, which transmits the motion down the inside of the upper arm outer tube 42. Motion DF3, rotation of the lower arm, is generated by motor 77, and transmitted through gear train 78 to a shaft running inside of the upper arm outer tube 42, to rotate the lower arm. Transfer of this inner rotation through the articulated arm joint is achieved using a double Cardan joint, which will be described in FIG. 8 hereinbelow. Finally, motion DF4 for operating the grasper jaws is obtained from motor 79 through gear train 70 to the innermost shaft within the upper arm outer shaft.

Figure 8:
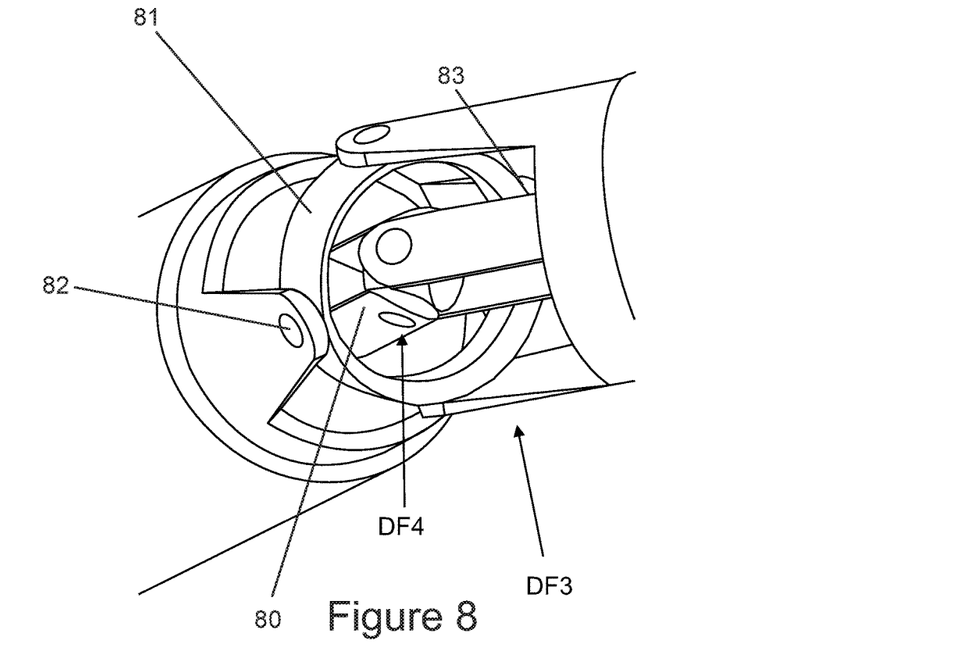
FIG. 8 shows a concentric system of Cardan joints allowing simultaneous power transmission through the articulated arm of the tool of FIGS. 2 to 7.

Reference is now made to FIG. 8, which illustrates schematically, according to a further preferred embodiment of the present invention, an arrangement for transmitting the rotary motion DF3 for operating the lower arm rotation, and the rotary motion DF4 for operating the grasper, through the joint of the articulated arm of the tool. A concentric double Cardan joint is used, the inner joint being of conventional design using a double yoke 80, and the outer joint using a ring 81 with the orthogonal hinges 82, 83, attached thereto to avoid interfering with the inner joint. Although a Cardan joint does not provide a smooth angular transfer of motion when the angle between the input and output shafts is large, since unlike other types of flexible joints such as a constant-velocity joints, it can be simply constructed in a concentric design, it becomes the joint of choice for application in the tools of the present invention.

The rotary motion transmitted down the centermost drive channel of the tool arms, used for operating the grasper at the end of the lower arm, has to be converted to linear motion in order to actuate the grasper. The actuating power is preferably originated as rotary motion because of the ease of production of rotary motion by means of a motor, and is also transmitted as rotary motion because of the ease with which it can traverse the joint in the articulated arm, using the concentric Cardan joint shown in FIG. 8.

Figure 9A:
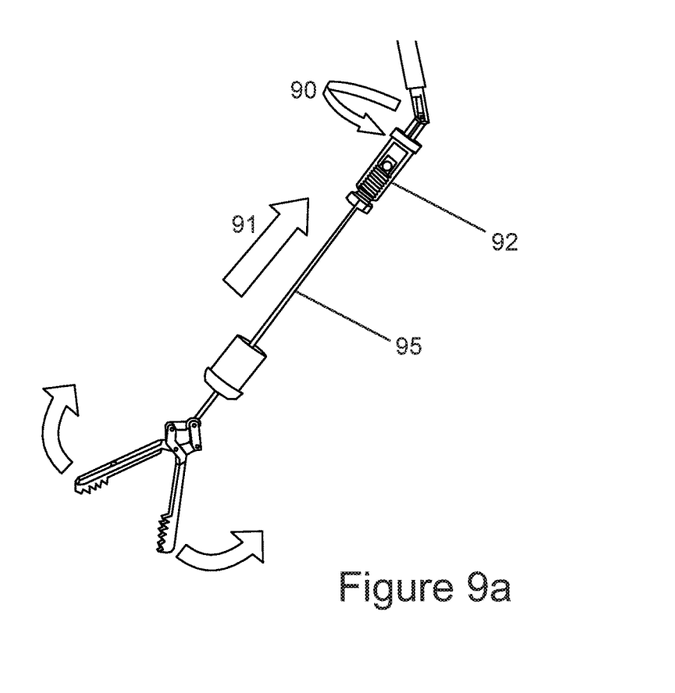
FIGS. 9a and 9b illustrate schematically an arrangement for converting the rotary motion shown in FIG. 8 into a linear motion required to actuate the jaws of the grasper.
Figure 9B:
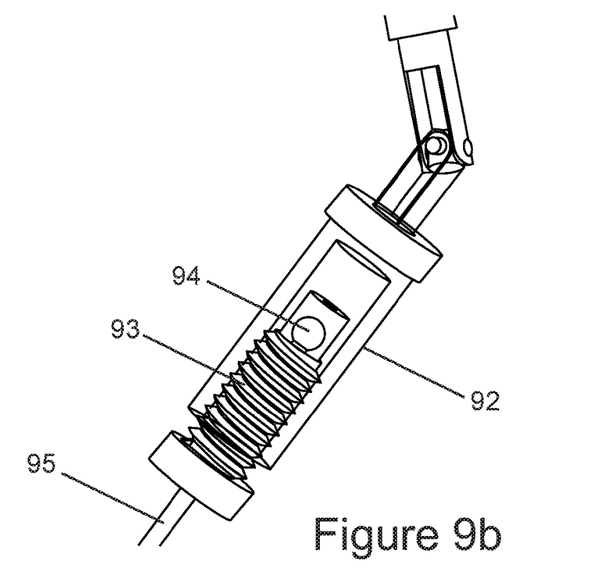

Reference is now made to FIGS. 9a and 9b, which illustrate schematically, according to a further preferred embodiment of the present invention, an arrangement for converting this rotary motion into the linear motion required to actuate the grasper. In FIG. 9a, there is shown an overall view of the internal motion actuating components within the lower arm. After traversing the articulated joint, the motion is converted from rotary 90 to linear 91 preferably in a screw motion converter 92, whose action is shown in detail in FIG. 9b hereinbelow. The linear motion 91 actuates the grasper jaws to open or close them, 93. The lower arm is not shown in FIG. 9a, but is understood to enclose the motion rod 94 and screw converter 92 shown therein, such that when the lower rod is rotated, the grasper also rotates.

Since the grasper operates directly on the patient's tissue, it is important that excessive clamping pressure is not applied thereto. In order to avoid such a situation, according to further preferred embodiments of this invention, one or more clutches are added to the rotary motion train before the screw converter, in order to limit the torque which can be applied, and hence the closure force of the grasper jaws. Additionally and preferably, in order to provide more tactile sensitivity for the surgeon, a force feedback loop can be applied to the grasper control, using a torque sensor, such that the surgeon can feel the apparent force being applied to grasp the tissue.

Reference is now made to FIG. 9b, which illustrates schematically a preferred internal construction of the screw motion converter shown in FIG. 9a. The actuating nut of the converter is an internal thread formed in the converter housing 92. As the converter housing is rotated, the screw 93 moves up or down depending on the direction of rotation. A ball 94 connected to the end of the actuator rod 95 of the grasper, is held captive but free to move within a cavity in the screw structure, and as the screw structure moves up and down, it pulls the ball with it, and hence the actuator rod 95. The rod can be prevented from turning with rotation of the converter housing by clamping the connector flange 96 in a housing which allows it to move up and down but not to rotate. Such an embodiment is shown in more detail in FIGS. 15a to 15c hereinbelow. Alternatively and preferably, instead of a ball 94 at the top end of the actuator rod, a shape such as a hexagon or square may be used to prevent the rod and screw from turning with rotation of the converter housing.

Figure 10:
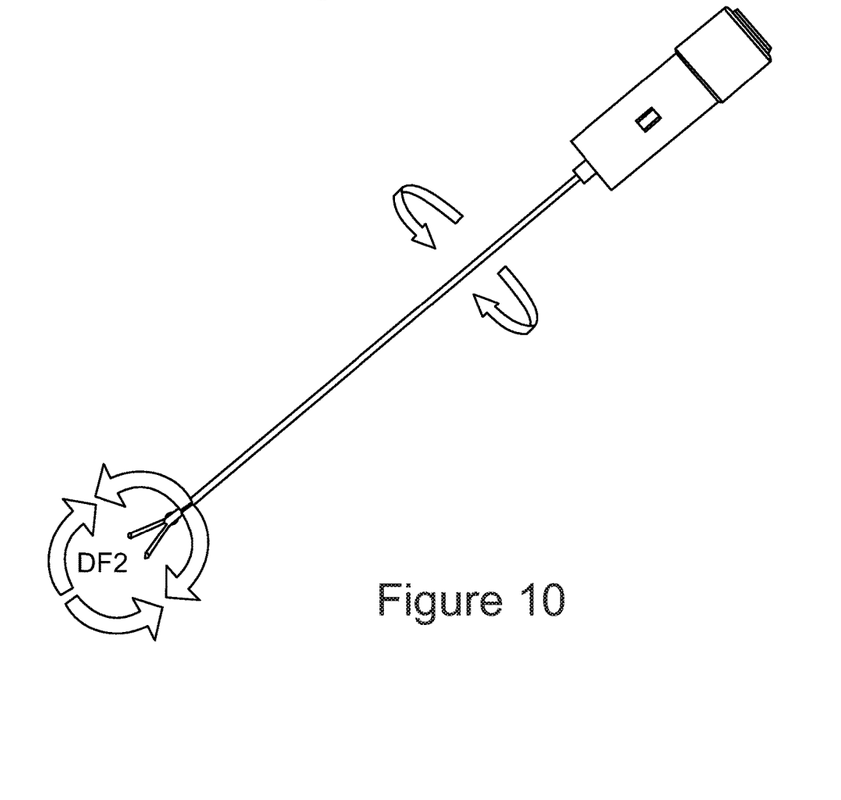
FIG. 10 is a close up schematic view of the motorized surgical tool, according to a further preferred embodiment of the present invention, held in the surgeon's left hand in FIGS. 1 and 2.

Reference is now made to FIG. 10, which is a close up schematic view of the motorized surgical tool, according to a preferred embodiment of the present invention, held in the surgeon's left hand 12 of FIGS. 1 and 2. The operation of the tool has been described in FIG. 2 hereinabove. In FIG. 10, the rotary motion DF1 and the grasper jaw actuation motion DF2 are shown.

Figure 11:
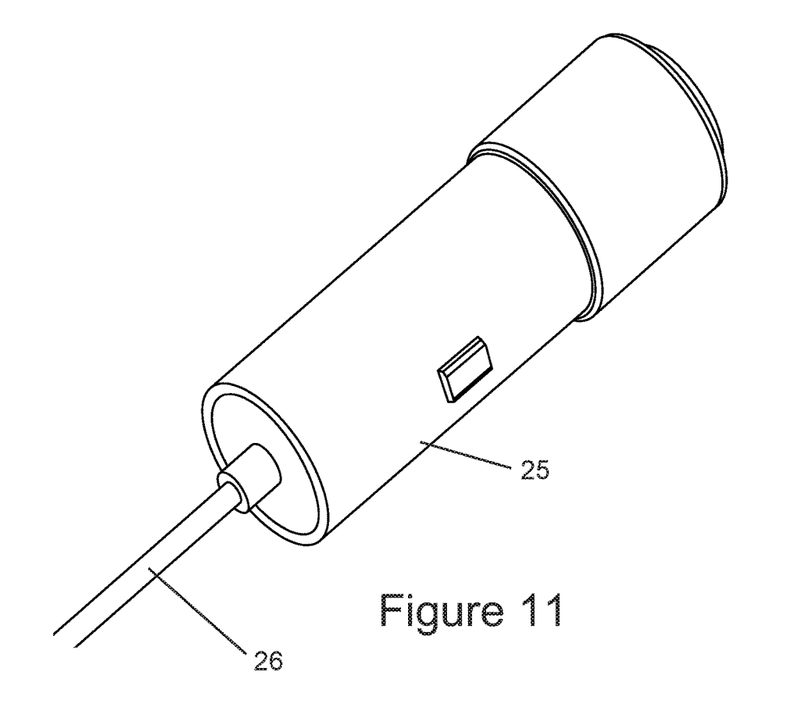
FIG. 11 is an external schematic view of the motor/gear housing of the preferred motorized tool shown in FIG. 10.

FIG. 11 is an external schematic view of the motor/gear housing 25 of the preferred motorized tool shown in FIG. 10, showing the actuating rod 26 projecting from its distal end.

Figure 12:
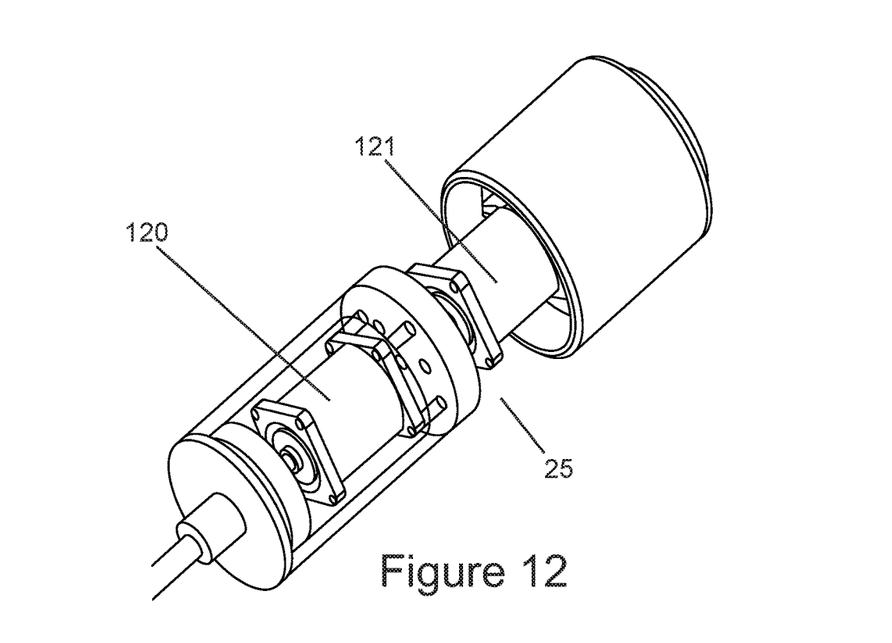
FIG. 12 is an internal view of the motor/gear housing of FIG. 11.

FIG. 12 is an internal view of the motor/gear housing 25 of FIG. 11, with the lower part of the outer casing removed, showing at its distal end, the motor 120 for providing the DF2 motion for the gripper, and at its proximal end, the motor 121 for providing the DF1 rotary motion of the tool.

Figure 13:
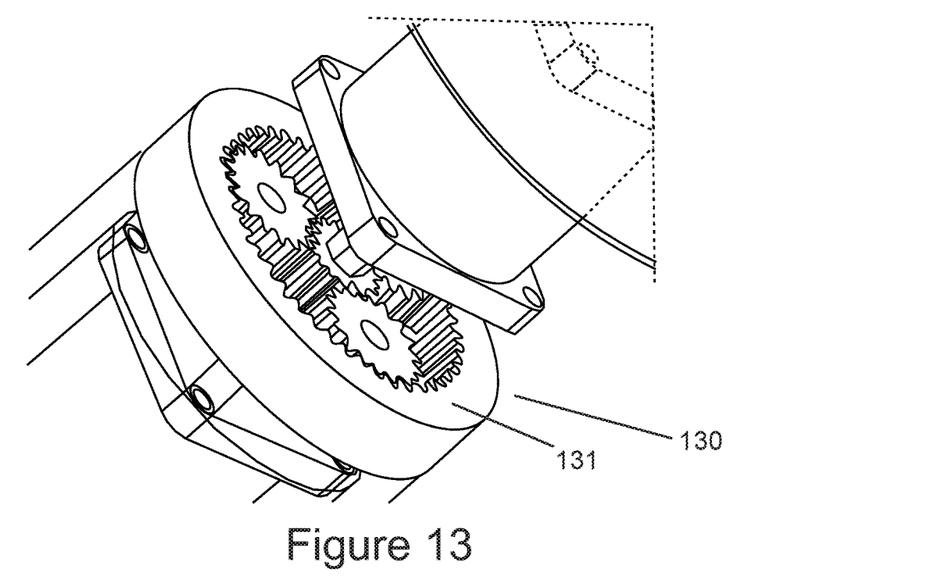
FIG. 13 is an internal view of a planetary gear cluster preferably used within the motor/gear housing of the embodiment of FIGS. 11 and 12.

Reference is now made to FIG. 13, which is an internal view of a planetary gear cluster 130 preferably used within the motor/gear housing of FIGS. 11 and 12, for increasing the torque and reducing the rotational speed of the motor 121 which provides the tool with the rotation motion DF1. The ring gear 131 acts as the output shaft of the planetary gear cluster, and is attached to the lower part of the motor/gear housing 25, to which is attached the actuating arm 26.

Figure 14:
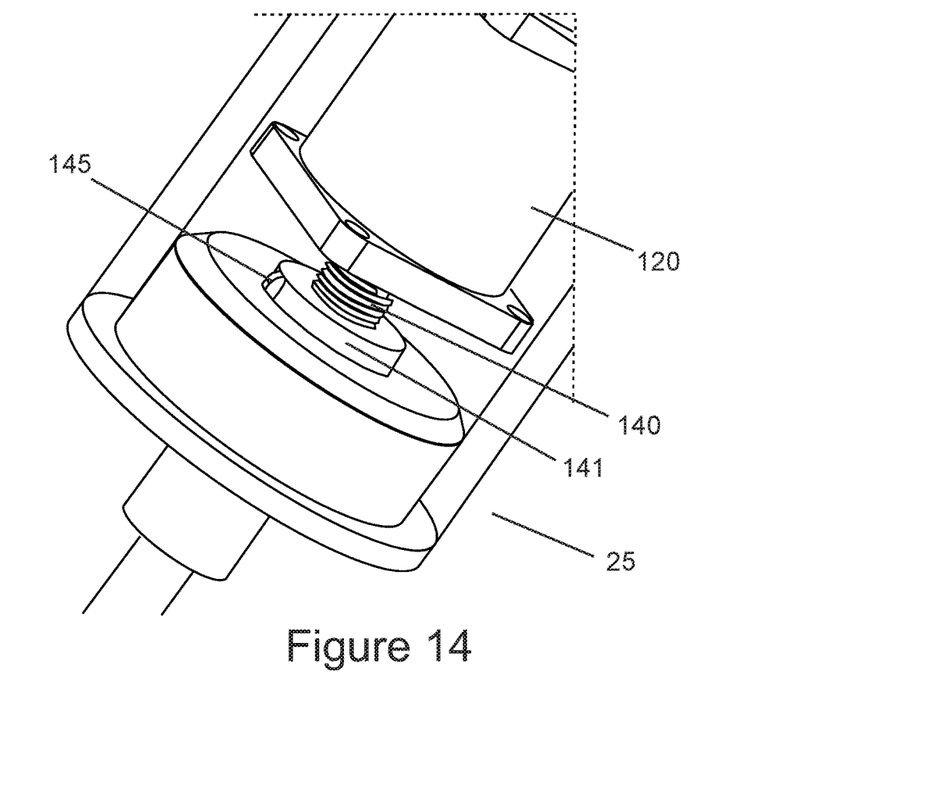
FIG. 14 shows the distal part of the motor/gear housing showing a screw mechanism for converting the rotary motor motion to linear motion.

FIG. 14 shows the distal part of the motor/gear housing 25, showing the screw mechanism for converting the rotary motor 120 motion to linear motion for actuating the grasper jaw motion DF2. The rotary motion applied to the screw 140 causes the nut 141 to move up and down within its cavity in the end plate 142 of the motor/gear housing, since it is constrained from turning by the flaps on its periphery.

Figure 15A:
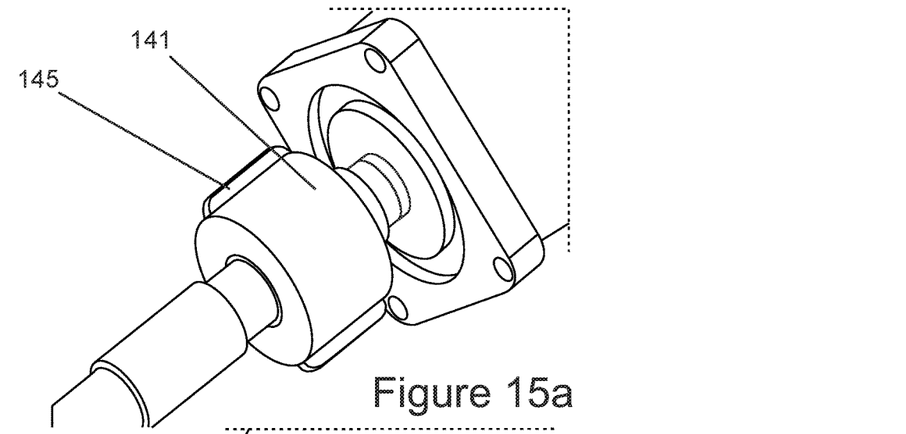
FIGS. 15a, 15b and 15c show more details of the screw mechanism of FIG. 14, for converting the rotary motor motion to linear motion.
Figure 15B:
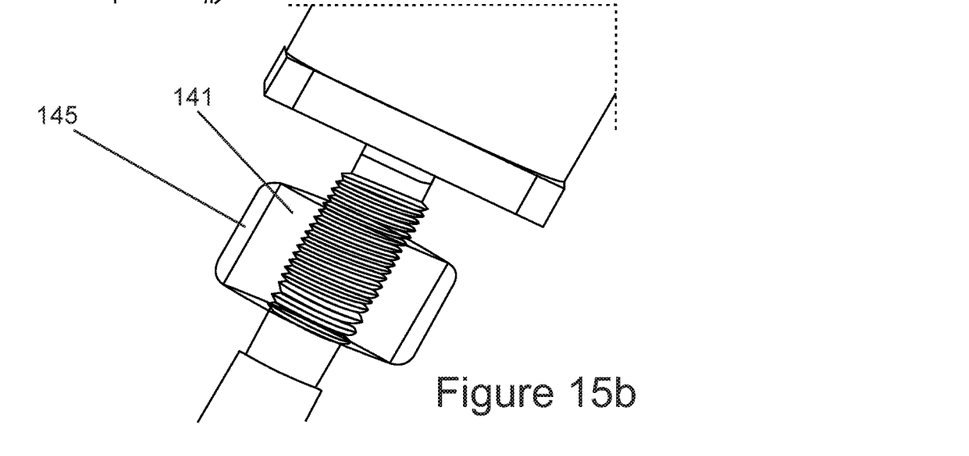
Figure 15C:
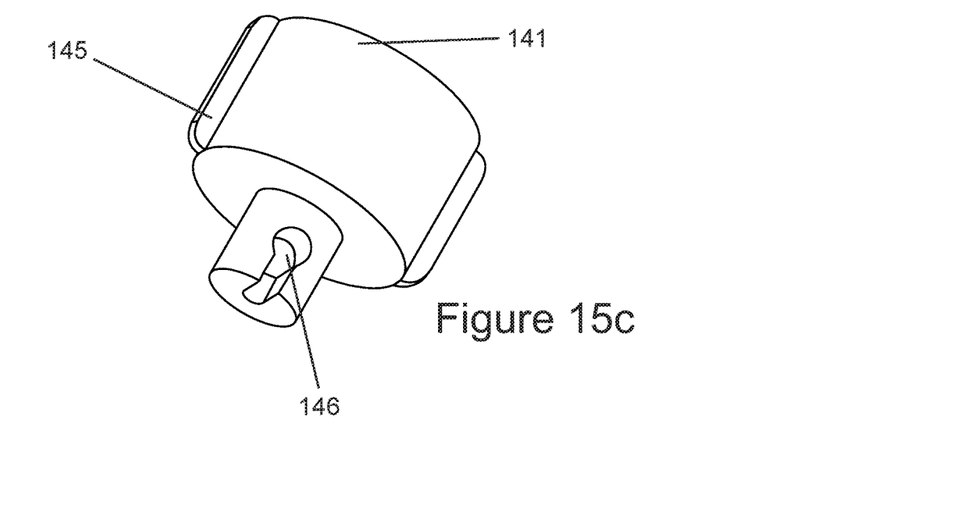

FIGS. 15a, b, c show more details of the screw mechanism of FIG. 14, for converting the rotary motor 120 motion to linear motion. FIG. 15a shows how the nut 141 is held stationary within the end plate of the motor/gear housing by its flaps 145. FIG. 15b is an X-ray view of the nut 141. FIG. 15c is a view of the distal end of the nut showing the cavity 146 for containing a ball at the proximal ends of the actuating rod, similar to the embodiment described in FIG. 9b.

Figure 16:
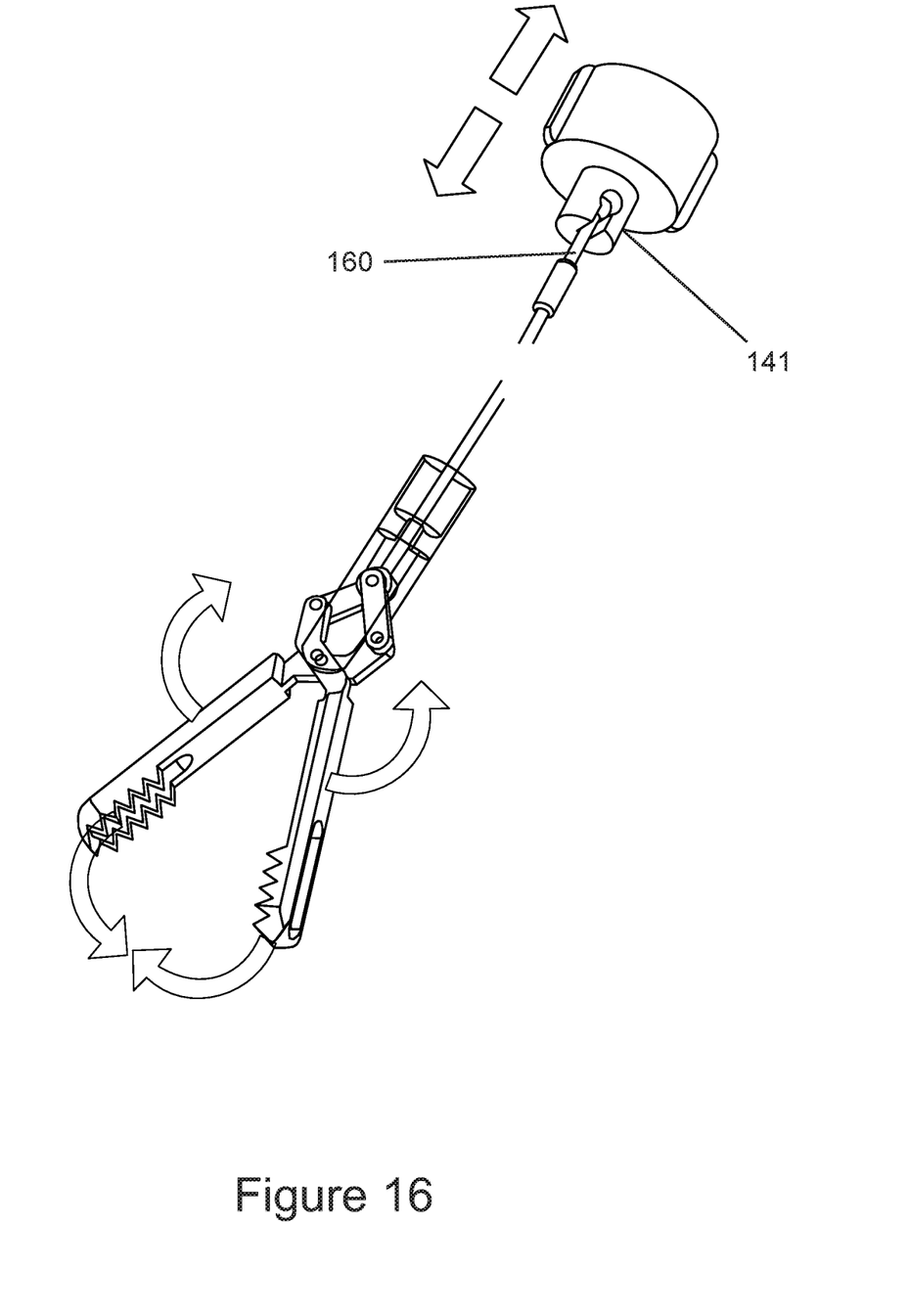
FIG. 16 shows the main parts of the linear mechanism that enables the opening and closing the jaws of the grasper of the tool of FIGS. 10 to 15c.

FIG. 16 shows the main parts of the linear mechanism that enables the opening and closing the jaws of grasper, from the nut 141, via the ball headed actuating rod 160 to the jaw actuating arms, providing the grasping motion DF2.

Figure 17:
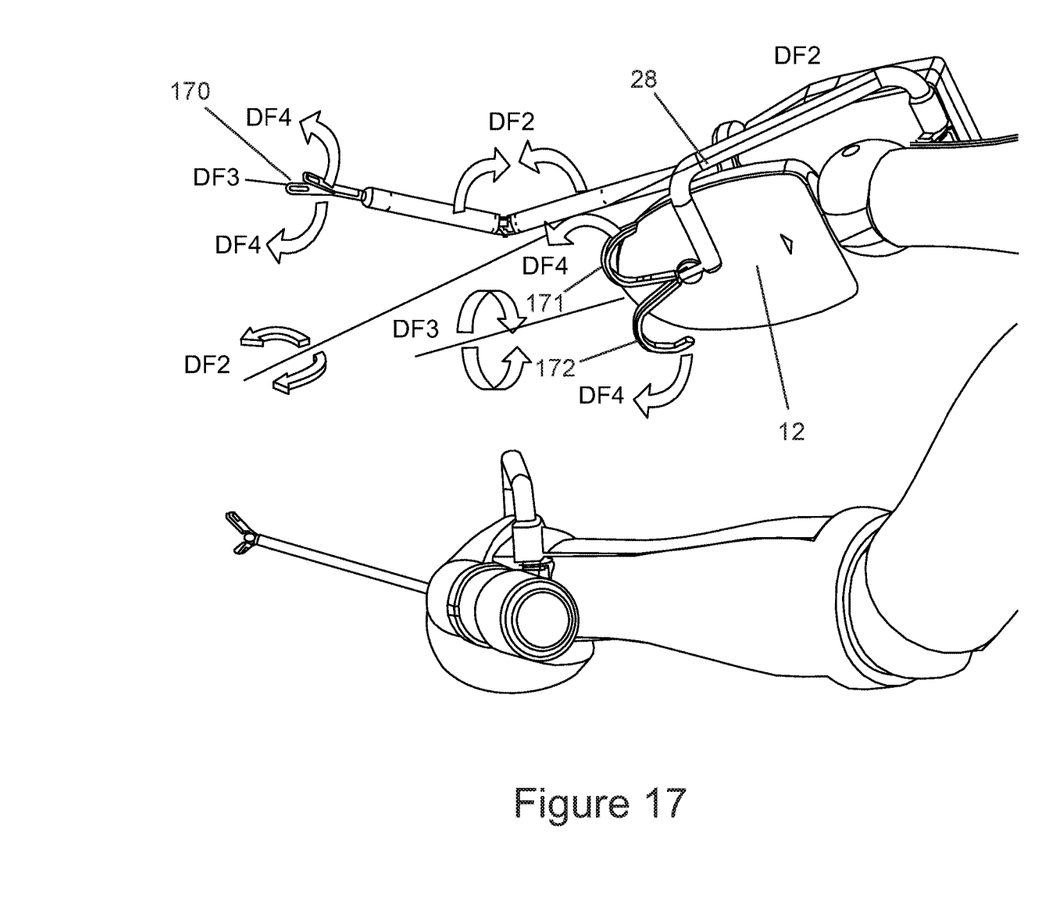
FIG. 17 is an overall view of the system from the surgeon's stance, showing the interface motions required for effecting the four separate motions enabled by the embodiment of the tool shown in FIG. 4.

Reference is now made to FIG. 17, which is an overall view of the system from the surgeon's stance, showing the four separate motions enabled by the embodiment of the tool shown in FIG. 4. The interface controls shown are an alternative embodiment from those shown in FIG. 6 hereinabove, but the operating principles remain the same. In the embodiment of FIG. 17, the surgeon's right hand 12 is holding the tool by the operating arm 28. The control for actuating the motion DF4 of the grasper jaws 170 comprises two, preferably thumb-operated, triggers 171, 172, for opening and closing the jaws. The rotation DF3 of the lower arm of the tool is accomplished in the preferred embodiment of FIG. 17 by rotation of the hand held triggers, those which actuate the jaw motion DF4. The bending motion DF2 of the articulated arm is accomplished by rotation of the operating arm 28 around its axis.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

The invention claimed is:

1. A hand-held motorized surgical instrument, comprising:
   a drive unit incorporating at least two motors and associated gear trains, said drive unit providing at least first and second concentric rotary motions, said drive unit being securable to a back of a hand or a forearm of a user thereby freeing a palm and fingers of said user to selectively engage an interface for controlling an operation of said drive unit;
   an end effector adapted to perform a surgical procedure; and
   at least a first set of first and second concentric tubes for transmitting said rotary motions, said first concentric tube providing rotary power to actuate said end effector, and said second concentric tube for rotating said end effector.

2. The hand-held motorized surgical instrument according to claim 1, further comprising a converter housing for converting at least one of said rotary motions to a linear motion.

3. The hand-held motorized surgical instrument according to claim 2 wherein said linear motion is utilized for actuating said end effector.

4. The hand-held motorized surgical instrument according to claim 1, further comprising a second set of first and second concentric tubes attached to said first set of first and second concentric tubes by means of flexible joints, such that rotary power transmitted by said first concentric tube of said first set is transferred to said first concentric tube of said second set, and rotary power transmitted by said second concentric tube of said first set is transferred to said second concentric tube of said second set, such that said first and second concentric rotary motions are transmitted through an articulated joint.

* * * * *